(12) United States Patent
Yamashita et al.

(10) Patent No.: US 9,598,477 B2
(45) Date of Patent: Mar. 21, 2017

(54) METHODS OF TREATING METABOLIC DISORDERS

(71) Applicant: Chubu University Educational Foundation, Kasugai-shi (JP)

(72) Inventors: Hitoshi Yamashita, Kasugai (JP); Tatsuya Kusudo, Kasugai (JP)

(73) Assignee: CHUBU UNIVERSITY EDUCATIONAL FOUNDATION, Kasugai-shi (JP)

( * ) Notice: Subject to any disclaimer, the term of this patent is extended or adjusted under 35 U.S.C. 154(b) by 0 days.

(21) Appl. No.: 14/421,903

(22) PCT Filed: Aug. 9, 2013

(86) PCT No.: PCT/JP2013/071591
§ 371 (c)(1),
(2) Date: Feb. 16, 2015

(87) PCT Pub. No.: WO2014/027608
PCT Pub. Date: Feb. 20, 2014

(65) Prior Publication Data
US 2015/0232522 A1    Aug. 20, 2015

(30) Foreign Application Priority Data

Aug. 17, 2012 (JP) ................... 2012-180905

(51) Int. Cl.
| | |
|---|---|
| C07K 14/00 | (2006.01) |
| C07K 14/47 | (2006.01) |
| A61K 38/00 | (2006.01) |
| A61K 45/00 | (2006.01) |
| G01N 33/50 | (2006.01) |
| A23L 1/305 | (2006.01) |
| A61K 48/00 | (2006.01) |

(52) U.S. Cl.
CPC .......... *C07K 14/4703* (2013.01); *A23L 1/305* (2013.01); *A61K 38/00* (2013.01); *C07K 14/00* (2013.01); *G01N 33/5023* (2013.01); *A23V 2002/00* (2013.01); *A61K 48/00* (2013.01); *G01N 2500/04* (2013.01)

(58) Field of Classification Search
CPC .... C07K 14/00; C07K 14/4703; A61K 38/00; A61K 48/00; G01N 33/5023; G01N 2500/04
See application file for complete search history.

(56) References Cited

U.S. PATENT DOCUMENTS 7,390,780 B2 *   6/2008   Huang .................. A61K 9/1272
                                                                435/5

FOREIGN PATENT DOCUMENTS

| WO | WO 2010/080985 A1 | 7/2010 |
| WO | WO 2011/126790 A1 | 10/2011 |
| WO | WO 2012/092049 A2 | 7/2012 |

OTHER PUBLICATIONS

Moolmuang, B., et al. CREG1 enhances p16INK4a-induced cellular senescence. Cell Cycle, 2011, vol. 10, No. 3, p. 518-530.*
Han, Y, et al. Adenovirus-mediated intra-arterial delivery of cellular repressor of E1A-stimulated genes inhibits neointima formation in rabbits after balloon injury. Journal of Vascular Surgery, 2008, vol. 48, No. 1, p. 202-209.*
https://www.nlm.nih.gov/medlineplus/metabolicdisorders.html, retreived on Jan. 27, 2016. Medline Plus entry for "Metabolic Disorder".*
B.B. Lowell et al. "Development of obesity in transgenic mice after genetic ablation of brown adipose tissue," Nature 366: 1993, pp. 740-742.
S. Enerbäck et al., "Mice lacking mitochondrial uncoupling protein are cold-sensitive but not obese," Nature 387: 1997, pp. 90-94.
Y. Kontani et al., "UCP1 deficiency increases susceptibility to diet-induced obesity with age," Aging Cell 4: 2005, pp. 147-155.
A. M. Cypess et al., "Identification and Importance of Brown Adipose Tissue in Adult Humans," New England Journal of Medicine 360: 2009, pp. 1509-1517.
J. Lin et al., "Metabolic control through the PGC-1 family of transcription coactivators," Cell Metabolism 1: 2005, pp. 361-370.
P. Seale et al., "PRDM16 controls a brown fat/skeletal muscle switch," Nature 454: 2008, pp. 961-967 and information sheet.
International Search Report dated Oct. 22, 2013, issued for PCT/JP2013/071591.
European Search Report, issued May 11, 2016 in connection with EP Application No./Patent No. 13879526.2/2886650.
Ya-Ling Han et al: "Secreted CREG inhibits cell proliferation mediated by mannose 6-phosphate/insulin-like growth factor II receptor in NIH3T3 fibroblasts", Genes to Cells, vol. 13, No. 9, Sep. 1, 2008 (Sep. 1, 2008), pp. 977-986, XP055266440, GB ISSN: 1356-9597, DOI: 10.1111/j.1365-2443.2008.01221.x.
Elizabeth Veal et al: "The secreted glycoprotein CREG enhances differentiation of NTERA-2 human embryonal carcinoma cells", Oncogene, vol. 19, No. 17, Jan. 1, 2000 (Jan. 1, 2000), pp. 2120-2128, XP055197445, DOI: 10.1038/sj.onc.1203529.
Alessandra Di Bacco et al: "The secreted glycoprotein CREG inhibits cell growth L, dependent on the mannose-6-phosphate/insulin-like growth factor II receptor", Oncogene, vol. 22, No. 35, Aug. 21, 2003 (Aug. 21, 2003), pp. 5436-5445, XP055197446, ISSN: 0950-9232, DOI: 10.1038/sj.onc.1206670.

(Continued)

*Primary Examiner* — Robert Landsman
*Assistant Examiner* — Bruce D Hissong
(74) *Attorney, Agent, or Firm* — Locke Lord, LLP; James E. Armstrong, IV; Nicholas R. Herrel

(57) ABSTRACT

The present invention addresses the problem of providing a means which is effective for the induction of the differentiation of a brown adipocyte and therefore enables a brown adipocyte to be used for and applied to, for example, the prevention/treatment of obesity or metabolic syndrome. Provided is a brown adipocyte differentiation-inducing agent containing, as an active ingredient, (1) CREG1 protein or (2) an expression vector carrying CREG1 gene.

9 Claims, 8 Drawing Sheets

(56) References Cited

OTHER PUBLICATIONS

Han Y et al: "Adenovirus-mediated intra-arterial delivery of cellular repressor of E1A-stimulated genes inhibits neointima formation in rabbits after, balloon injury", Journal of Vascular Surgery, C.V. Mosby Co., St. Louis, MO, US, vol. 48, No. 1, Jul. 1, 2008 (Jul. 1, 2008), pp. 201-209, XP022760329, ISSN: 0741-5214, DOI: 10.1016/J.JVS.2008.01.061.

* cited by examiner

FIG. 8

|  | LacZ (n=3) | Creg1 (n=3) | p |
|---|---|---|---|
| BW (g) | 26.5±0.9 | 23.9±0.9 | 0.0546 |
| E-WAT | 0.229±0.022 | 0.144±0.009 | 0.011 |
| R-WAT | 0.035±0.005 | 0.020±0.002 | 0.021 |
| Liver | 1.911±0.075 | 1.430±0.144 | 0.021 |

SEQUENCE LISTING

```
<160> NUMBER OF SEQ ID NOS: 3

<210> SEQ ID NO 1
<211> LENGTH: 220
<212> TYPE: PRT
<213> ORGANISM: Homo sapiens

<400> SEQUENCE: 1

Met Ala Gly Leu Ser Arg Gly Ser Ala Arg Ala Leu Leu Ala Ala Leu
1               5                   10                  15

Leu Ala Ser Thr Leu Leu Ala Leu Leu Val Ser Pro Ala Arg Gly Arg
                20                  25                  30

Gly Gly Arg Asp His Gly Asp Trp Asp Glu Ala Ser Arg Leu Pro Pro
            35                  40                  45

Leu Pro Pro Arg Glu Asp Ala Ala Arg Val Ala Arg Phe Val Thr His
        50                  55                  60

Val Ser Asp Trp Gly Ala Leu Ala Thr Ile Ser Thr Leu Glu Ala Val
65                  70                  75                  80

Arg Gly Arg Pro Phe Ala Asp Val Leu Ser Leu Ser Asp Gly Pro Pro
                85                  90                  95

Gly Ala Gly Ser Gly Val Pro Tyr Phe Tyr Leu Ser Pro Leu Gln Leu
            100                 105                 110

Ser Val Ser Asn Leu Gln Glu Asn Pro Tyr Ala Thr Leu Thr Met Thr
        115                 120                 125

Leu Ala Gln Thr Asn Phe Cys Lys Lys His Gly Phe Asp Pro Gln Ser
    130                 135                 140

Pro Leu Cys Val His Ile Met Leu Ser Gly Thr Val Thr Lys Val Asn
145                 150                 155                 160

Glu Thr Glu Met Asp Ile Ala Lys His Ser Leu Phe Ile Arg His Pro
                165                 170                 175

Glu Met Lys Thr Trp Pro Ser Ser His Asn Trp Phe Phe Ala Lys Leu
            180                 185                 190

Asn Ile Thr Asn Ile Trp Val Leu Asp Tyr Phe Gly Gly Pro Lys Ile
        195                 200                 205

Val Thr Pro Glu Glu Tyr Tyr Asn Val Thr Val Gln
    210                 215                 220

<210> SEQ ID NO 2
<211> LENGTH: 189
<212> TYPE: PRT
<213> ORGANISM: Homo sapiens

<400> SEQUENCE: 2

Arg Gly Gly Arg Asp His Gly Asp Trp Asp Glu Ala Ser Arg Leu Pro
1               5                   10                  15

Pro Leu Pro Pro Arg Glu Asp Ala Ala Arg Val Ala Arg Phe Val Thr
```

|  |  | 20 |  |  |  | 25 |  |  |  | 30 |  |
|---|---|---|---|---|---|---|---|---|---|---|---|
| His | Val | Ser | Asp | Trp | Gly | Ala | Leu | Ala | Thr | Ile | Ser | Thr | Leu | Glu | Ala |
|  |  |  | 35 |  |  |  | 40 |  |  |  | 45 |  |  |  |  |
| Val | Arg | Gly | Arg | Pro | Phe | Ala | Asp | Val | Leu | Ser | Leu | Ser | Asp | Gly | Pro |
|  | 50 |  |  |  |  | 55 |  |  |  |  | 60 |  |  |  |  |
| Pro | Gly | Ala | Gly | Ser | Gly | Val | Pro | Tyr | Phe | Tyr | Leu | Ser | Pro | Leu | Gln |
| 65 |  |  |  |  | 70 |  |  |  |  | 75 |  |  |  |  | 80 |
| Leu | Ser | Val | Ser | Asn | Leu | Gln | Glu | Asn | Pro | Tyr | Ala | Thr | Leu | Thr | Met |
|  |  |  |  | 85 |  |  |  |  | 90 |  |  |  |  | 95 |  |
| Thr | Leu | Ala | Gln | Thr | Asn | Phe | Cys | Lys | Lys | His | Gly | Phe | Asp | Pro | Gln |
|  |  |  | 100 |  |  |  |  | 105 |  |  |  |  | 110 |  |  |
| Ser | Pro | Leu | Cys | Val | His | Ile | Met | Leu | Ser | Gly | Thr | Val | Thr | Lys | Val |
|  |  | 115 |  |  |  |  | 120 |  |  |  |  | 125 |  |  |  |
| Asn | Glu | Thr | Glu | Met | Asp | Ile | Ala | Lys | His | Ser | Leu | Phe | Ile | Arg | His |
|  | 130 |  |  |  |  | 135 |  |  |  |  | 140 |  |  |  |  |
| Pro | Glu | Met | Lys | Thr | Trp | Pro | Ser | Ser | His | Asn | Trp | Phe | Phe | Ala | Lys |
| 145 |  |  |  |  | 150 |  |  |  |  | 155 |  |  |  |  | 160 |
| Leu | Asn | Ile | Thr | Asn | Ile | Trp | Val | Leu | Asp | Tyr | Phe | Gly | Gly | Pro | Lys |
|  |  |  |  | 165 |  |  |  |  | 170 |  |  |  |  | 175 |  |
| Ile | Val | Thr | Pro | Glu | Glu | Tyr | Tyr | Asn | Val | Thr | Val | Gln |  |  |  |
|  |  |  | 180 |  |  |  |  | 185 |  |  |  |  |  |  |  |

<210> SEQ ID NO 3
<211> LENGTH: 2048
<212> TYPE: DNA
<213> ORGANISM: Homo sapiens

<400> SEQUENCE: 3

| ggcggggcct | gggcgcgccg | agctccggct | gggtccctgc | aggtcttggg | gcccgggact | 60 |
| cttcctggag | acaccgccat | ggccgggcta | tcccgcgggt | ccgcgcgcgc | actgctcgcc | 120 |
| gccctgctgg | cgtcgacgct | gttggcgctg | ctcgtgtcgc | ccgcgcgggg | tcgcggcggc | 180 |
| cgggaccacg | gggactggga | cgaggcctcc | cggctgccgc | cgctaccacc | ccgcgaggac | 240 |
| gcggcgcgcg | tggcccgctt | cgtgacgcac | gtctccgact | ggggcgctct | ggccaccatc | 300 |
| tccacgctgg | aggcggtgcg | cggccggccc | ttcgccgacg | tcctctcgct | cagcgacggg | 360 |
| cccccgggcg | cgggcagcgg | cgtgccctat | ttctacctga | gcccgctgca | gctctccgtg | 420 |
| agcaacctgc | aggagaatcc | atatgctaca | ctgaccatga | ctttggcaca | gaccaacttc | 480 |
| tgcaagaaac | atggatttga | tccacaaagt | ccccttgtg  | ttcacataat | gctgtcagga | 540 |
| actgtgacca | aggtgaatga | aacagaaatg | gatattgcaa | agcattcgtt | attcattcga | 600 |
| caccctgaga | tgaaaacctg | gccttccagc | cataattggt | tctttgctaa | gttgaatata | 660 |
| accaatatct | gggtcctgga | ctactttggt | ggaccaaaaa | tcgtgacacc | agaagaatat | 720 |
| tataatgtca | cagttcagtg | aagcagactg | tggtgaattt | agcaaacactt | atgaagtttc | 780 |
| ttaaagtggc | tcatacacac | ttaaaaggct | taatgtttct | ctggaaagcg | tcccagaata | 840 |
| ttagccagtt | ttctgtcaca | tgctggtttg | tttgcttgct | tgtttacttg | cttgtttacc | 900 |
| aatagagttg | acctgttatt | ggatttcctg | gaagatgtgg | tagctacttt | tttcctattt | 960 |
| tgaagccatt | ttcgtagaga | aatatccttc | actataatca | aataagtttt | gtcccatcaa | 1020 |
| ttccaaagat | gtttccagtg | gtgctcttga | agaggaatga | gtaccagttt | taaattgccc | 1080 |
| attggcattt | gaaggtagtt | gagtatgtgt | tctttattcc | tagaagccac | tgtgcttggt | 1140 |
| agagtgcatc | actcaccaca | gctgcctcct | gagctgcctg | agcctggtgc | aaaaggattg | 1200 |

-continued

```
gcccccatta tggtgcttct gaataaatct tgccaagata gacaaacaat gatgaaactc    1260
agatggagct tcctactcac gttgatttat gtctcacaat cctgggtatt gttaattcaa    1320
catagggtga aactatttct gataaagaac ttttgaaaaa cttttttatac tctaaagtga   1380 tactcagaac aaaagaaagt cataaaactc ctgaatttaa tttccccacc taagtcgaaa    1440
cagtattatc aaaacacatg tgcacacaga ttattttttg gctccaaaac tggattgcaa    1500
aagaaagagg agaagaatat tttgtgtgtt cctggtattc ttttataagt aaagtttacc    1560
caggcatgga ccagcttcag ccagggacaa aatcccctcc caaaccactc tccacagctt    1620
tttaaaaata cttctactct taacaattac ctaaggcttc ctcaactgcc ccaaatctct    1680
taatagcttc tagtgctgct acaatctaag tcaggtcacc agagggaaga gaacatggca    1740
ttaaaagaat cacatcttca gaagagaaga cactaatatt attacccata tacatgattt    1800
cagaagatga cataagattc ctcttaaaga ggaaatgtca ggaatcaagc cactgaatcc    1860
ttaaagagaa aagttgaata tgagtcattg tgtctgaaaa ctgcaaagtg aacttaactg    1920
agatccagca aacaggttct gtttaagaaa aataatttat actaaattta gtaaaatgga    1980
cttcttattc aaagcatcaa taattaaaag aattatttta atgaaaaaaa aaaaaaaaa    2040 aaaaaaaa                                                              2048
```

METHODS OF TREATING METABOLIC DISORDERS

TECHNICAL FIELD

The present invention relates to a brown adipocyte differentiation-inducing agent and use thereof. The present application claims priority based on Japanese Patent Application No. 2012-180905 filed on Aug. 17, 2012, and the whole content of the patent application is herein incorporated by reference.

BACKGROUND ART

In the adipocytes of mammals, white adipocytes, which store energy as triglycerides, and brown adipocytes, which generate heat by utilizing triglycerides to thereby contribute to the control of body temperature, are present. Hibernators and rodents, which have developed brown adipose tissues, can live by adjusting themselves to even a cold environment at about 5° C. In the case of human, brown adipose tissues are observed in the peripheries of the shoulder blades in a newborn infant, but the brown adipocytes decrease in accordance with growth.

On the other hand, brown adipocytes consume excess energy as heat by producing heat, and thus have attracted interests in relation to obesity and diabetes mellitus. Actually, significant development of obesity was observed in a transgenic mouse from which brown adipocytes had been ablated genetically (Non-patent Document 1). Furthermore, the present inventors generated a mouse with deficiency of mitochondria uncoupling protein (UCP1; uncoupling protein 1), which is a major molecule for the heat generation in brown adipocytes (Non-patent Document 2), and reported that this mouse developed diet-induced obesity with aging (Non-patent Document 3). It has been considered that, unlike experimental animals such as mouse, human brown adipocytes disappear with aging, and thus have substantial little roles in human. However, it was recently clarified that brown adipocytes are also present in adult humans, although the amount thereof is small, and the existing amount thereof inversely relates to a degree of obesity and a blood glucose level (Non-patent Document 4), and thus brown adipocytes have gained a great deal of attention since the induction of differentiation of brown adipocytes would be useful for the prevention and treatment of obesity and metabolic syndrome (Non-patent Document 5). On the other hand, with respect to transcriptional regulators that control the differentiation of brown adipocytes, it has been clarified that PGC1α (Non-patent Document 6) and PRDM16 (Non-patent Document 7) and the like play important roles.

PRIOR ART DOCUMENT

Non-Patent Document

Non-patent Document 1: Nature 366: 740-742, 1993
Non-patent Document 2: Nature 387: 90-94, 1997
Non-patent Document 3: Aging Cell 4: 147-155, 2005
Non-patent Document 4: N Engl J Med 360: 1509-1517, 2009
Non-patent Document 5: Science and Technology Trends, June 2009 (Ministry of Education, Culture, Sports, Science and Technology, National Institute of Science and Technology Policy, Science and Technology Trends Research Center)
Non-patent Document 6: Cell Metab 1: 361-370, 2005
Non-patent Document 7: Nature 454: 961-967, 2008

SUMMARY OF INVENTION

Problem to be Solved by the Invention

However, any application example in which brown adipocytes are induced in a human by utilizing PGC1α or PRDM16 has not been reported. Furthermore, it is expected that there are molecules that are positioned on the upper stream or down stream of PGC1α or PRDM16 in the control of the differentiation of adipocytes and act on the induction of the differentiation of brown adipocytes, and thus the identification of those unknown genes is an important problem. Therefore, the present invention aims at providing an effective means for the induction of the differentiation of brown adipocytes, thereby contribute to the utilization and application of brown adipocytes to the prevention and treatment of obesity and metabolic syndrome, and the like.

Means for Solving Problem

The present inventors found a cellular repressor of E1A-stimulated genes 1 (Creg1) as one of novel genes whose expression rises in accordance with the differentiation of brown adipocytes in the process of a study on the mechanism of the development of brown adipose tissue under a cold environment. Furthermore, the inventors clarified that Creg1 actually acts on the induction of differentiation of brown adipocytes (see Examples), and consequently completed the present invention shown below.

[1] A brown adipocyte differentiation-inducing agent containing the following (1) or (2) as an active ingredient:
(1) CREG1 protein;
(2) an expression vector carrying CREG1 gene.

[2] The brown adipocyte differentiation-inducing agent according to [1], wherein the CREG1 protein contains the amino acid sequence of SEQ ID NO: 1 or 2, or an amino acid sequence that is equivalent to the amino acid sequence.

[3] The brown adipocyte differentiation-inducing agent according to [1], wherein the CREG1 gene contains a nucleotide sequence shown in SEQ ID NO: 3, or a nucleotide sequence that is equivalent to the nucleotide sequence.

[4] A composition for the treatment or prevention of metabolic disorders or the related disease thereof, containing the brown adipocyte differentiation-inducing agent according to any one of [1] to [3].

[5] The composition according to [4], wherein the metabolic disorders or the related disease thereof is obesity, diabetes mellitus, lipid abnormality, arteriosclerosis or metabolic syndrome.

[6] The composition according to [4] or [5], which is a medicament, a quasi drug or a food.

[7] A method for treating metabolic disorders or the related disease thereof, including a step of administrating a medicament containing the following (1) or (2) as an active ingredient to a patient or potential patient of metabolic disorders or the related disease thereof:
(1) CREG1 protein;
(2) an expression vector carrying CREG1 gene.

[8] A method for screening a brown adipocyte differentiation-inducing substance, including examining whether or not a test substance shows an action to increase the expression or secretion of CREG1.

[9] The screening method according to [8], including the following steps (i) to (iii):

(i) a step of culturing cells in which CREG1 is expressed, in the presence of a test substance;

(ii) a step of measuring an expression level or secretion level of CREG1 in the cells; and (iii) a step of determining the effectiveness of the test substance based on the measurement result, wherein an increase of the expression level or secretion level of CREG1 indicate the effectiveness.

[10] The screening method according to [9], wherein the effectiveness in the step (iii) is determined by preparing cells that have been cultured under a condition that is identical with the condition in the step (i) except that the condition is under the absence of the test substance (control group), and making a comparison with the expression level or secretion level of CREG1 in the control group.

BRIEF DESCRIPTION OF THE DRAWINGS

FIG. 8 shows the effect of Creg1 induction on the tissue weight in ApoE-knockout mice given a high fat diet. At 14 days after the induction of Creg1 expression, the body weight and the weights of epididymal white adipose tissue (E-WAT), retroperitoneal white adipose tissue (R-WAT) and liver were measured.

DESCRIPTION OF EMBODIMENTS

1. Brown Adipocyte Differentiation-Inducing Agent

Figure 1:
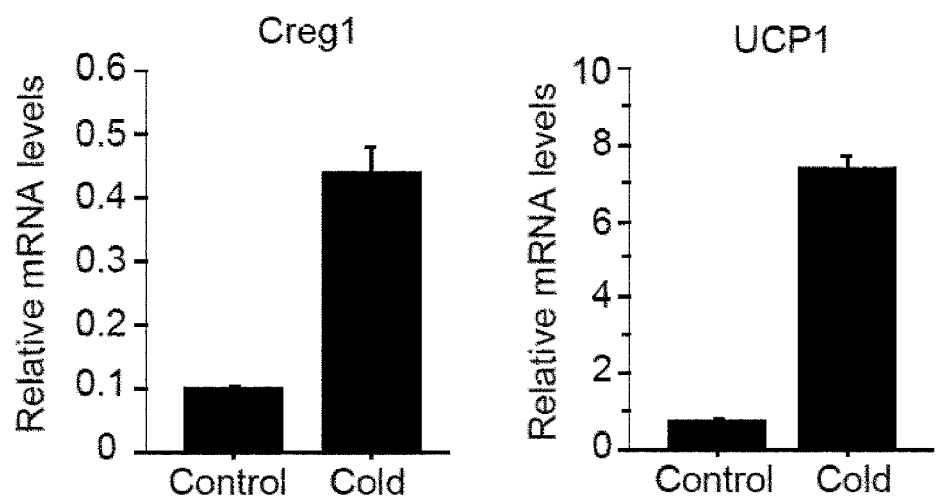
FIG. 1 shows the changes of the expression levels of Creg1 and UCP1 mRNAs in brown adipose tissues of mice exposed to cold. Left: the relative expression levels of Creg1 mRNA, right: the relative expression levels of UCP1 mRNA.

The first aspect of the present invention relates to a brown adipocyte differentiation-inducing agent (hereinafter also referred to as "differentiation-inducing agent" for the sake of convenience of explanation). The "brown adipocyte differentiation-inducing agent" refers to an agent that acts on cells having a potency to differentiate into brown adipocytes (i.e., progenitor cells or stem cells, typically muscle and brown fat progenitor cells or adipocyte precursor cells) to work the cells to differentiate into brown adipocytes. When the brown adipocyte differentiation-inducing agent is used, differentiation into brown adipocytes is promoted, and the number of the brown adipocytes consequently increases.

The differentiation-inducing agent of the present invention contains (1) CREG1 protein or (2) an expression vector carrying CREG1 gene as an active ingredient, based on the finding brought by the study of the present inventors, i.e., the fact that a cellular repressor of E1A-stimulated genes 1 (in the following explanation, the molecule is represented by its gene symbol "CREG1" according to the practices) functions as a brown adipocyte differentiation-inducing factor. Although the differentiation-inducing agent of the present invention generally contains only (1) or (2), but this does not inhibit the differentiation-inducing agent to contain both components.

(1) CREG1 Protein

CREG1 is a secretory glycoprotein, and is known to be involved in the proliferation and differentiation of cells (see Veal E, Eisenstein M, Tseng Z H, Gill G Mol Cell Biol. 1998 September; 18 (9): 5032-41, Di Bacco, A., Gill, G Oncogene (2003), Sacher, M., Di Bacco, A., Lunin, V. V., Ye, Z., Wagner, J., Gill, G, Cygler, M. Proc. Natl. Acad. Sci. U.S.A. (2005) and the like), but the details of the physiological role thereof is unclear. The amino acid sequence of CREG1 and a nucleotide sequence encoding therefor are respectively shown in SEQ ID NO: 1 (GenPept (NCBI), ACCESSION: NP_003842, DEFINITION: protein CREG1 precursor [*Homo sapiens*].) and SEQ ID NO: 3 (GenBank (NCBI), ACCESSION: NM 003851, DEFINITION: *Homo sapiens* cellular repressor of E1A-stimulated genes 1 (CREG1), mRNA.) of the Sequence List.

As the CREG1 protein as one of the active ingredients in the present invention, besides the precursor (SEQ ID NO: 1), a mature body in which the signal peptide has been cleaved (SEQ ID NO: 2) and only a specific region (i.e., a fragment) may also be used.

A polypeptide containing an amino acid sequence that is equivalent to the amino acid sequence of each of the above-mentioned proteins (precursor, mature body and the like) can also be used as the CREG1 protein. The "equivalent amino acid sequence" as used herein refers to an amino acid sequence that partially differs from an amino acid sequence as a criterion (for example, SEQ ID NO: 1 or 2), but the difference does not substantially affect the function of the protein (an action to induce differentiation into brown adipocytes). Therefore, functional and substantial identity is recognized between the amino acid sequence that serves as a criterion and the amino acid sequence that is equivalent to that amino acid sequence. In order to determine the presence or absence of functional and substantial identity, for example, it is sufficient to confirm that there is no substantial difference between the two amino acid sequences in the action and effect to induce the differentiation of brown adipocytes by using the experimental system described in the following Examples (evaluation by cultured cells or animals).

The "partial difference of an amino acid sequence" means occurrence of variation (change) in an amino acid sequence by deletion or substitution of one to several amino acids (upper limit is, for example, three, five, seven or ten) constituting an amino acid sequence, or addition or insertion of one to several amino acids (upper limit is, for example, three, five, seven or ten), or combination thereof. The difference of an amino acid sequence herein is acceptable as long as the above function does not drastically deteriorate. As long as this condition is satisfied, a position at which an amino acid sequence is different is not particularly limited, and the difference may be generated in plural positions. "Plurality" herein is, for example, the number that corresponds to less than about 30% of the entire amino acids, preferably the number that corresponds to less than about 20%, more preferably the number that corresponds to less than about 10%, further more preferably the number that corresponds to less than about 5%, and most preferably the number that corresponds to less than about 1%. That is, an equivalent amino acid sequence has an identity of, for example, about 70% or more, preferably about 80% or more, more preferably about 90% or more, further more preferably about 95% or more, and most preferably about 99% or more of the reference amino acid sequence.

It is preferable that the difference between the reference amino acid sequence and the equivalent amino acid sequence is occurred by preservative amino acid substitution. The "preservative amino acid substitution" herein refers to substitution of an amino acid residue into an amino acid residue having a side chain with similar nature. Amino acid residues are classified into several families by side chains thereof, such as basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), n-branched side chains (e.g., threonine, valine, and isoleucine), and aromatic side chains (e.g., tyrosine, phenylalanine, tryptophan, and histidine). Preservative amino acid substitution is preferably substitution between amino acid residues in the same family.

By the way, an identity (%) of two amino acid sequences or two nucleotide sequences (hereinafter, "two sequences" is used as the term including them) can be determined by the following procedure, for example. First, two sequences are aligned so that the sequences can be optimally compared (for example, a gap may be introduced in the first sequence to optimize alignment with the second sequence). When a molecule (amino acid residue or nucleotide) at a specific position in the first sequence is the same as a molecule at a position corresponding thereto in the second sequence, the molecules in these positions would be the same. An identity of two sequences is a function of the number of identical positions common in the two sequences (i.e. identity (%)=number of identical positions/total number of positions×100), and the number and sizes of gaps required for optimization of alignment should also be preferably taken into consideration.

Comparison of two sequences and determination of identity thereof are feasible using a mathematical algorithm. Specific examples of the mathematical algorithm applicable to comparison of sequences include an algorithm described in Karlin and Altschul (1990) Proc. Natl. Acad. Sci. USA 87: 2264-68 and modified in Karlin and Altschul (1993) Proc. Natl. Acad. Sci. USA 90: 5873-77, but are not limited thereto. Such an algorithm is incorporated into the NBLAST program and XBLAST program (version 2.0) described in Altschul et al. (1990) J. Mol. Biol. 215:403-10. In order to obtain a nucleotide sequence equivalent to a nucleic acid molecule of the present invention, for example, BLAST nucleotide search may be carried out by the NBLAST program at a score of 100 and a wordlength of 12. In order to obtain an amino acid sequence equivalent to a reference amino acid sequence, for example, BLAST polypeptide search may be carried out by the XBLAST program at a score of 50 and a wordlength of 3. In order to obtain a gap alignment for comparison, Gapped BLAST described in Altschul et al. (1997) Amino Acids Research 25(17): 3389-3402 is available. When BLAST and Gapped BLAST are employed, a default parameter of a corresponding program (such as XBLAST and NBLAST) can be used. See, for example, the web page of NCBI for detail. Examples of another mathematical algorithm applicable to comparison of sequences include the algorithm described in Myers and Miller (1988) Comput Appl Biosci. 4:11-17. Such an algorithm is incorporated in the ALIGN program available from, for example, the GENESTREAM network server (IGH Montpellier, France) or the ISREC server. When the ALIGN program is used for comparison of amino acid sequences, for example, the PAM120 residue mass table is used, a gap length penalty can be set to 12 and a gap penalty can be set to 4.

An identity of two amino acid sequences can be determined with the GAP program of the GCG software package using Blossom 62 matrix or PAM250 matrix, and setting a gap load to 12, 10, 8, 6 or 4 and a gap length load to 2, 3 or 4. Further, a homology of two nucleic acid sequences can be determined with the GAP program of the GCG software package (available from http://www.gcg.com) setting a gap load to 50 and a gap length load to 3.

CREG1 can be easily prepared by using a standard gene engineering technology, a molecular biological technology, a biochemical technology or the like with referring to the sequence information disclosed by this specification or the attached sequence list. For example, CREG1 can be prepared by using suitable host cells (for example, E. coli, yeast, mammalian cells and the like) transformed by a DNA encoding for CREG1, and recovering the protein expressed in the transformant. The recovered protein is suitably purified depending on the purpose. If CREG1 is obtained as a recombinant protein by this way, various modifications are possible. For example, if a DNA encoding for CREG1 and other suitable DNA are inserted into the same vector, and a recombinant protein is produced by using this vector, CREG1 formed of a recombinant protein to which an optional peptide or protein is connected can be obtained. Furthermore, addition of a sugar chain and/or a lipid, or modification such that processing of a N-terminal or a C-terminal is generated may be conducted. By the above-mentioned modification, extraction of a recombinant protein, simplification of purification, or addition of a biological function or the like is possible.

From the viewpoints of qualitative homogeneity and purity and the like, it is preferable to prepare CREG1 by a gene engineering technology. However, the method for preparing CREG1 is not limited to a method by a gene engineering technology. For example, CREG1 can also be prepared from a natural material (for example, blood or a biological tissue) by a standard technology (crushing, extraction, purification or the like).

(2) Expression Vector Carrying CREG1 Gene

In one embodiment of the present invention, an expression vector carrying CREG1 gene is used as an active ingredient. The "expression vector" herein refers to a vector capable of introducing a polynucleotide inserted therein into a desired cell (host cell) and expressing the polypeptide in the cell. In the expression vector of the present invention, CREG1 gene is carried in a state capable of expressing. The kind of vector is not particularly limited as long as CREG1 gene can be introduced into a target cell and expressed in the cell. The vector herein includes a virus vector and a nonvirus vector. A gene introduction method using a virus vector skillfully utilizes a phenomenon of infection of a cell with a virus, and a high gene introduction efficiency can be obtained. As the virus vector, an adenovirus vector, an adeno-associated virus vector, a retrovirus vector, a lentivirus vector, a herpesvirus vector, a Sendai virus vector, and the like, have been developed.

As a nonvirus vector, a liposome, a positively charged liposome (Feigner, P. L., Gadek, T. R., Holm, M. et al., Proc. Natl. Acad. Sci., 84:7413-7417, 1987), HVJ (Hamagglutinating virus of Japan)-liposome (Dzau, V. J., Mann, M., Morishita, R. et al., Proc. Natl. Acad. Sci., 93:11421-11425, 1996, Kaneda, Y., Saeki, Y. & Morishita, R., Molecular Med. Today, 5:298-303, 1999), and the like have been developed. The expression vector of the present invention can be constructed as such a nonvirus vector. YAC vector, BAC vector and the like can also be used.

In an adeno-associated virus vector, a retrovirus vector, and a lentivirus vector, foreign genes incorporated into a vector are incorporated into a host chromosome, and stable and long-term expression can be expected. Since the retrovirus vector requires cell division for incorporation of a virus genome into a host chromosome, this vector is not appropriate for gene introduction into a nondividing cell. On the other hand, a lentivirus vector and an adeno-associated virus vector cause incorporation of foreign genes into host chromosomes after infection also in nondividing cells. Therefore, these vectors are effective for expressing foreign genes stably and for a long time in nondividing cells.

Each virus vector can be prepared by following a reported method or using a commercially available special kit. For example, preparation of an adenovirus vector can be carried out by a COS-TPC method or a full-length DNA introduction method. The COS-TPC method is a method for preparing a recombinant adenovirus by transfecting a recombinant cosmid in which a desired cDNA or an expression cassette are incorporated and a parent virus DNA-terminal protein complex (DNA-TPC) to 293 cells at the same time and utilizing homologous recombination generated in the 293 cells (Miyake, S., Makimura, M., Kanegae, Y., Harada, S., Takamori, K., Tokuda, C., and Saito, I. (1996) Proc. Natl. Acad. Sci. USA, 93, 1320.). On the other hand, the full-length DNA introduction method is a method for producing a recombinant adenovirus by performing a restriction digestion treatment on a recombinant cosmid inserted with a desired gene, thereafter transfecting the product to 293 cells (Miho Terashima, Saki Kondo, Yumi Kanegae, and Izumi Saito (2003) Experimental Medicine 21 (7) 931). The COS-TPC method can be performed with the Adenovirus Expression Vector Kit (Dual Version) (TAKARA BIO INC.) and Adenovirus genome DNA-TPC (TAKARA BIO INC.). Further, the full-length DNA introduction method can be performed with Adenovirus Expression Vector Kit (Dual Version) (TAKARA BIO INC.).

On the other hand, a retrovirus vector can be prepared by the following procedure. First, virus genomes (gag, pol, and env genes) other than packaging signal sequences between LTR (Long Terminal Repeat) present on the both ends of a virus genome are removed, and a desired gene is inserted therein. The thus constructed virus DNA is introduced in a packaging cell constitutionally expressing gag, pol, and env genes. With this introduction, only a vector RNA having a packaging signal sequence is incorporated in a virus particle and a retrovirus vector is produced.

As a vector obtained by application or improvement in an adenovirus vector, a vector in which specificity is improved by modification of a fiber protein (specific infection vector) and a gutted vector from which improvement in an expression efficiency of a desired gene can be expected (helper-dependent vector), and the like, have been developed. The expression vector of the present invention can be constructed as such a virus vector.

In a preferred embodiment, CREG1 gene which is inserted in an expression vector comprises the nucleotide sequence of SEQ ID NO: 3. A DNA equivalent to the nucleotide sequence (herein after referred to as an "equivalent DNA") can be used as CREG1 gene. The "equivalent nucleotide sequence" herein refers to a nucleotide sequence having a partial difference from the reference nucleotide sequence (SEQ ID NO: 3), in which the difference, however, gives no substantial effect on a function of the protein encoded by the nucleotide sequence. Specific examples of an equivalent DNA include a DNA that hybridizes to a nucleotide sequence which is complementary to the reference nucleotide sequence under stringent conditions. The "stringent conditions" herein refers to conditions where a so-called specific hybrid is formed, but a non-specific hybrid is not formed. Such stringent conditions have been known to a skilled person, and can be set in reference to, for example, Molecular Cloning (Third Edition, Cold Spring Harbor Laboratory Press, New York) and Current protocols in molecular biology (edited by Frederick M. Ausubel et al., 1987). The stringent conditions include, for example, such conditions that incubation is carried out at about 42° C. to about 50° C. using a hybridization solution (50% formamide, 10×SSC (0.15 M NaCl, 15 mM sodium citrate, pH 7.0), 5×Denhardt solution, 1% SDS, 10% dextran sulfate, 10 µg/ml of denatured salmon sperm DNA, 50 mM phosphate buffer (pH 7.5)), and then washing is carried out at about 65° C. to about 70° C. with 0.1×SSC and 0.1% SDS. Preferable stringent conditions include, for example, such conditions that 50% formamide, 5×SSC (0.15 M NaCl, 15 mM sodium citrate, pH 7.0), 1×Denhardt solution, 1% SDS, 10% dextran sulfate, 10 µg/ml of denatured salmon sperm DNA, 50 mM phosphate buffer (pH 7.5) is used as a hybridization solution.

Other specific examples of an equivalent DNA include a nucleotide sequence containing substitution, deletion, insertion, addition, or inversion of one or plural nucleotides based on the reference nucleotide sequence, and encoding a protein effective for induction of brown adipocyte differentiation. Substitution and deletion of nucleotides may occur in a plurality of sites. "Plurality" herein indicates, for example, 2 to 40 nucleotides, preferably 2 to 20 nucleotides, and more preferably 2 to 10 nucleotides although depending on a position and a kind of an amino acid residue in a conformation of a protein encoded by the polynucleotide. Such an equivalent DNA can be obtained by modifying a DNA having the reference nucleotide sequence so as to contain substitution, deletion, insertion, addition and/or inversion of nucleotides, utilizing introduction of variation, for example, a restriction enzyme treatment, a treatment with exonuclease, DNA ligase, or the like, a site-specific mutation introduction method (Molecular Cloning, Third Edition, Chapter 13, Cold Spring Harbor Laboratory Press, New York), and a random mutation introduction method (Molecular Cloning, Third Edition, Chapter 13, Cold Spring Harbor Laboratory Press, New York). An equivalent DNA can also be obtained by other methods such as exposure to ultraviolet radiation.

Other examples of an equivalent DNA include a DNA in which such above-mentioned difference in nucleotides originated from a polymorphism typified by SNP (single nucleotide polymorphism).

CREG1 gene can be prepared by using a standard gene engineering technology, a molecular biological technology, a biochemical technology or the like with referring to the sequence information disclosed by this specification or the attached sequence list. For example, CREG1 gene can be isolated (and amplified) from a human cDNA library by suitably utilizing an oligonucleotide probe/primer that can be specifically hybridized to a CREG1 gene. As the oligonucleotide probe/primer, for example, a DNA that is complementary to the nucleotide sequence shown in SEQ ID NO: 3 or a continuous part thereof is used. The oligonucleotide probe/primer can be easily synthesized by using a commercially available automatic DNA synthetic apparatus or the like. With respect to the method for the preparation of the library used for preparing CREG1 gene, for example, Molecular Cloning, Third Edition, Cold Spring Harbor Laboratory Press, New York serves as a reference.

If a cDNA library derived from cells of a mammal other than human (for example, monkey, mouse, rat, pig, cattle) is used instead of a human cDNA library, an equivalent DNA can be prepared.

2. Composition Containing Brown Adipocyte Differentiation-Inducing Agent

Brown adipocytes are special cells that consume excess energy by combusting triglycerides, and it has been clarified that the decrease thereof causes the onset of obesity and metabolic syndrome. Therefore, increasing of brown adipocytes serves as an effective means for the prevention/treatment of obesity, and metabolic disorders or the related disease thereof such as metabolic syndrome. Therefore, the second aspect of the present invention is to provide a composition for treating or preventing metabolic disorders or the related disease thereof.

(1) Pharmaceutical Composition/Quasi Drug Composition

The composition of the present invention is preferably provided in the form of a medicament, a quasi drug or a food. Specifically, the present invention provides, as preferable embodiments, a pharmaceutical composition, a quasi drug composition and a food composition comprising the differentiation-inducing agent of the present invention as an active ingredient. Specific examples of "metabolic disorders or the related disease thereof" to be treated or prevented by the composition of the present invention (hereinafter referred to as "target disease" for the sake of convenience of explanation) are obesity, diabetes mellitus, lipid abnormality, arteriosclerosis and metabolic syndrome. The "obesity" herein generally refers to a state in which adipose tissues are excessively accumulated in the body. In the present specification, the term "obesity" shall be widely interpreted, and the concept thereof includes obesity disease. The "obesity disease" refers to a pathological condition that is expected to have or have in the future a health disorder (complication) that is caused by or relates to obesity and thus medically requires weight reduction. As a method for determining obesity, for example, a method using BMI (body mass index), which is internationally and widely used, is used as a scale. BMI is a numerical value obtained by dividing a body weight (kg) by a square of a body height (m) (BMI=body weight (kg)/body height $(m)^2$). BMI<18.5 is determined to be a low body weight (underweight), 18.5≤BMI<25 is determined to be a normal body weight (normal range), 25≤BMI<30 is determined to be obese degree 1 (preobese), 30≤BMI<35 is determined to be obese degree 2 (obese class I), 35≤BMI<40 is determined to be obese degree 3 (obese class II), and 40<BMI is determined to be obese degree 4 (obese class III) (WHO). Furthermore, there is another determination method in which a standard body weight (ideal body weight) of a Japanese adult human is calculated from the following formula: standard body weight (kg)=body height $(m)^2 \times 22$, by utilizing BMI, and a state in which an actually-measured body weight exceeds 120% of the standard body weight (calculated value) is deemed as obesity. However, since the standard body weight (ideal body weight) differs in every individual depending on difference in gender, age or lifestyle habit, and the like, it is considered to be inappropriate to determine obesity by this method in a single uniform way.

"Metabolic syndrome" refers to a state in which insulin resistance, arteriosclerosis-evoked lipoprotein abnormality and hypertension are coexisting based on obesity and accumulation of visceral fats, and thus the risk of acquiring cardiovascular diseases has increased. Regarding the criteria for the diagnosis of metabolic syndrome, the following diagnostic criteria were prepared on April 2005 by eight Japanese societies of internal medicine in union (Japan Atherosclerosis Society, Japan Society for the study of Obesity, Japan Diabetes Society, Japanese Society of Hypertension, Japanese Circulation Society, Japanese Society of Internal Medicine, Japanese Society of Nephrology and Japanese Society on Thrombosis and Hemostasis).

<Diagnostic Criteria by Eight Societies Including Japanese Society of Internal Medicine and the Like>

Two or more of (b) to (d) are satisfied in addition to the following (a).

(a) Abdominal circumference: 85 cm or more in male, 90 cm or more in female (b) Triglycerides is 150 mg/dl or more and/or HDL-C is lower than 40 mg/dl (c) Blood pressure is 130/85 mmHg or more (d) Fasting blood glucose level is 110 mg/dl or more In addition, the International Diabetes Federation (IDF) prepared the following worldwide unified diagnostic criteria.

<Diagnostic Criteria by International Diabetes Federation (IDF)>

Two or more of (b) to (e) are satisfied in addition to the following (a).

(a) Abdominal circumference: 90 cm or more in male, 80 cm or more in female (b) Triglycerides is 150 mg/dl or more (c) Fasting blood glucose level is 100 mg/dl or more (d) HDL-C: lower than 40 mg/dl in male, lower than 45 mg/dl in female (e) Blood pressure is 130/85 mmHg or more The "medicament" and "quasi drug" in the present invention are agent compositions that show a treatment or preventive effect on a target disease. The treatment effect includes alleviating a symptom or associated symptom that is characteristic to a target disease (alleviation of a symptom), inhibiting or retarding the deterioration of a symptom, or the like. The latter can be interpreted as one of preventive effects in that increase in severity is prevented. Thus, a treatment effect and a preventive effect are concepts that partially overlap and thus are difficult to be captured by clearly distinguishing, and an actual advantage obtained by doing so is little. A typical preventive effect is to inhibit or retard the expression (onset) or recrudescence of a symptom or pathological condition that is characteristic to a target disease. The "medicament" and "quasi drug" fall within the pharmaceutical composition or quasi drug composition of the present invention as long as they show a certain treatment effect or preventive effect, or both of these effects, on a target disease.

The formulation of the pharmaceutical composition or quasi drug composition of the present invention may use a common procedure. When formulated, other components which are acceptable for formulation (for example, a carrier, an excipient, a disintegrating agent, a buffering agent, an emulsifying agent, a suspending agent, a soothing agent, a stabilizer, a preservative, an antiseptic, and a normal saline solution) may be added. Examples of the excipient include lactose, starch, sorbitol, D-mannitol, and white sugar. Examples of the disintegrating agent include starch, carboxymethyl cellulose, and calcium carbonate. Examples of the buffering agent include phosphates, citrates, and acetates. Examples of the emulsifying agent include gum arabic, sodium alginate, and tragacanth. Examples of the suspending agent include glycerol monostearate, monostearic acid aluminum, methyl cellulose, carboxymethyl cellulose, hydroxymethyl cellulose, and sodium lauryl sulfate. Examples of the soothing agent include benzyl alcohol, chlorobutanol, and sorbitol. Examples of the stabilizer include propylene glycol, and ascorbic acid. Examples of the preservative include phenol, benzalkonium chloride, benzyl alcohol, chlorobutanol, and methylparaben. Examples of the antiseptic include benzalkonium chloride, paraoxybenzoic acid, and chlorobutanol.

The form of formulation is not particularly limited. For example, the pharmaceutical composition or quasi drug composition of the present invention is provided as pellets, a powder, fine pellets, granules, capsules, a syrup, an injection, an external preparation, and a suppository.

An active ingredient in an amount necessary for obtaining an expected treatment effect or preventive effect (i.e., a treatment effective amount) is contained in the pharmaceutical composition of the present invention. Similarly, the active ingredient in an amount necessary for obtaining an expected treatment effect or preventive effect (i.e., a treatment effective amount) is incorporated in the quasi drug composition of the present invention. The amount of the active ingredient contained in the pharmaceutical composition or quasi drug composition of the present invention generally differs depending on the dosage form or shape, and the amount of the active ingredient is preset within a range of, for example, from about 0.1% by weight to about 99% by weight, so that a desired dose can be achieved.

The pharmaceutical composition and quasi drug composition of the present invention are each applied to a subject by an oral or parenteral manner (intravenous, intraarterial, subcutaneous, intramuscular or intraperitoneal injection, transdermal, transnasal, transmucosal, application, or the like) depending on the dosage form and shape thereof. The "subject" herein is not especially limited, and includes human and mammals other than human (pet animals, domestic animals, experimental animals are included, and specific examples are mouse, rat, guinea pig, hamster, monkey, cattle, pig, goat, sheep, dog, cat, chicken, quail and the like). In preferable embodiments, the subject to be applied is a human.

The dose/usage of the pharmaceutical composition or quasi drug composition of the present invention is established to achieve the expected treatment effects. For the establishment of the treatment effective dose, in general, the symptoms, the age, sex, and body weight of the patient, and other factors are taken into consideration. Those skilled in the art can establish an appropriate dose in consideration of these factors. The administration schedule may be, for example, once to several times a day, once every two days, or once every three days. For the making of the administration schedule, the disease state of the patient, and the expected duration of the effect of the active ingredient may be taken into consideration.

Here, in the case when an expression vector carrying CREG1 gene is used as an active ingredient, it is preferable to formulate by combining with a pharmaceutically acceptable medium. The "pharmaceutically acceptable medium" refers to a substance that gives an advantage or benefit in relation to the administration, storage and the like of an expression vector without substantially affecting the medicinal effect of the expression vector (i.e., a treatment or preventive effect on a target disease). As the "pharmaceutically acceptable medium", deionized water, ultrapure water, saline, phosphate buffer saline (PBS), a 5% aqueous dextrose solution and the like can be exemplified. Other components such as a suspending agent, a soothing agent, a stabilizer (albumin, Prionex (registered trademark, Pentapharm Japan) and the like), a preservative and an antiseptic agent may be incorporated in the composition of the present invention.

In the case when the expression vector carrying CREG1 gene is in the form of a virus vector, it is preferable to use a biologically compatible polyol (such as poloxamer 407) in combination. By using the polyol, the transduction rate of the virus vector can rise to 10 to 100 times (March et al., Human Gene Therapy 6: 41-53, 1995). Therefore, if the polyol is used in combination, the dose of the virus vector can be suppressed to be low. In addition, the polyol may be used as a component of the pharmaceutical composition of the present invention, or the polyol (or a composition containing the polyol) may be prepared separately from the pharmaceutical composition of the present invention. In the latter case, the polyol (or a composition containing the polyol) is administered in combination when the pharmaceutical composition of the present invention is administered.

As is apparent from the above-mentioned description, the present application also provides a method for treating or preventing metabolic disorders or the related disease thereof, including administering a treatment effective amount of the pharmaceutical composition of the present invention to a patient or a potential patient (a person who is likely to be affected with the disease in the future).

(2) Food Composition

As mentioned above, one an embodiment of the present invention is a food composition containing the differentiation-inducing agent of the present invention. As examples of "food composition" in the present invention, general foods (grain, vegetables, edible meat, various processed foods, confectionery products, milk, soft drinks, alcohol beverages and the like), nutritious supplement foods (supplements, nutritious supplement drinks and the like), food additives, foods for pet animals and nutritious supplement foods for pet animals can be exemplified. In the case of a nutritious supplement food or food additive, it can be provided in the shape of a powder, a granular powder, a tablet, a paste, a liquid or the like. By providing in the form of a food composition, it becomes easy to take the active ingredient of the present invention on a daily basis or continuously.

It is preferable that the food composition of the present invention contains the active ingredient in an amount at which a treatment or preventive effect can be expected. The addition amount can be defined with consideration for the pathological condition, health state, age, gender, body weight and the like of a person who is a subject of use of the food composition.

3. Method for Screening Brown Adipocyte Differentiation-Inducing Substance

The third aspect of the present invention relates to a method for screening a brown adipocyte differentiation-inducing substance. The compound selected by the screening method of the present invention is prospective as an active ingredient for a brown adipocyte differentiation-inducing agent, and can be used for the treatment or prevention of metabolic disorders and the related disease thereof. In the screening method of the present invention, based on the finding that "enhancement of the expression of CREG1 is effective as a means for inducing differentiation into brown adipocytes", the effectiveness of a test substance is judged by using that "increase of the expression level of CREG1 is observed" as an indication. Specifically, the screening method of the present invention is characterized by that whether or not the test substance shows an action of increasing the expression level of CREG1. In an embodiment of the present invention, the following steps are carried out.

(i) a step of culturing cells in which CREG1 is expressed, in the presence of a test substance;

(ii) a step of measuring an expression level or secretion level of CREG1 in the cells; and (iii) a step of determining the effectiveness of the test substance based on the measurement result, wherein an increase of the expression level or secretion level of CREG1 indicates the effectiveness.

In the step (i), cells in which CREG1 is expressed (hereinafter referred to as "CREG1-expressed cells") are prepared, and these cells are cultured in the presence of a test substance. As these cells, adipocytes, hepatocytes, renal cells, skin cells or the like can be used. Cells that have been newly prepared from a living body or passaged cells thereof may be used, or a commercially available cell strain or the like may be used. Cells that have been engineered so as to forcedly express CREG1 (genetically engineered cells) can also be used. The species of origin for the cells are not especially limited. Examples of the organism species include mouse, rat, hamster, monkey and human.

Specific examples of preferable cells can include HepG2 cells, which are cells derived from human liver. As a result of examination of Creg1 expression in various cell strains, the present inventors have confirmed that HepG2 cells produce Creg1. Furthermore, since it is considered that one of major organs for the production of Creg1 is a liver, HepG2 cells are considered to be preferable cell strain as cells for screening.

As the test substance, organic compounds or inorganic compounds having various molecular sizes can be used. As examples of the organic compounds, nucleic acids, peptides, proteins, lipids (simple lipids, composite lipids (phosphoglyceride, sphingolipids, glycosylglycerides, cerebrosides and the like), prostaglandins, isoprenoids, terpenes, steroids, polyphenols, catechins, Vitamins (B1, B2, B3, B5, B6, B7, B9, B12, C, A, D, E and the like) can be exemplified. Existing components such as medicaments and nutrition foods and candidate components are also one of preferable test substances. A plant extraction liquid, a cell extraction liquid, a culture supernatant or the like may also be used as the test substance. It is also possible to examine the interaction, synergistic action and the like between test substances by simultaneously adding two or more kinds of test substances. The test substance may be from a natural substance, or may be a synthesized substance. In the latter case, an effective screening system can be constructed by, for example, utilizing a technology of combinatorial synthesis.

In order to culture CREG1-expressed cells in the presence of the test substance, for example, it is sufficient to seed the CREG1-expressed cell on a culture dish, and add the test substance to the culture medium, or to replace with a culture medium to which the test substance has been added, after a predetermined time (for example, 10 minutes to 1 week) has passed. It is also possible to carry out addition of the test substance or replacing with the culture medium to which the test substance has been added, immediately after the seeding. Furthermore, it is also possible to use a culture medium to which the test substance has been added in advance, so that "a state in which the test substance is present in the culture medium" is formed simultaneously with the seeding.

The culturing time in the presence of the test substance is not especially limited, and is set to, for example, from 10 minutes to 72 hours, preferably from 30 minutes to 24 hours. An optimal culturing time can be determined by a preliminary experiment.

The matters that are not mentioned in the present specification (culture medium, culturing temperature and the like) may follow general culturing conditions for the culturing of the cells used. The culturing conditions may be determined by referring to previous reports and books, or through preliminary experiments. The culturing temperature is generally 37° C.

In the step (ii), the CREG1 expression level or secretion level of the CREG1-expressed cells that have undergone the step (i), i.e., the CREG1-expressed cells that have been cultured for a predetermined time in the presence of the test substance, is measured. The method for measuring the CREG1 expression level is not especially limited. For example, the measuring can be conducted by quantifying the mRNA amount of CREG1 gene by RT-PCR, or by immunologically measuring the amount of CREG1 protein (for example, by Western blotting).

In the step (iii), the effectiveness of the test substance is determined based on the measurement result in the step (ii). In the present invention, as an indication showing that the test substance is effective, "the increase of the expression level or secretion level of CREG1 is observed" is adopted. Specifically, in the case when the increase of the expression level or secretion level of CREG1 is observed, the test substance is determined to be effective, whereas in the case when the increase of the expression level or secretion level of CREG1 is not observed, the test substance is determined to be ineffective. In the case when plural test substances are used, the effectivenesses of the respective test substances can be compared and evaluated based on the degrees of the increase of the expression levels or secretion levels.

An effective test substance is selected based on the result determined in the step (iii). Generally, CREG1-expressed cells that have been cultured in the absence of the test substance (the other conditions are identical with the conditions in step (1)) (hereinafter referred to as "control group") is prepared as a comparative subject, and the CREG1 expression level or secretion level thereof is also measured in parallel. Furthermore, whether or not the expression level or secretion level of CREG1 has been increased by the test substance is judged by comparing the CREG1 expression level or secretion level of the control group with the CREG1 expression level or secretion level of the test group. By determining the effectiveness of the test substance by comparing with the control group by this way, a determination result with higher reliability can be obtained.

In the case when the substance selected by the screening method of the present invention has a sufficient medicinal effect, the substance can be directly used as the active ingredient for the brown adipocyte differentiation-inducing agent. On the other hand, in the case when the substance does not have a sufficient medicinal effect, the substance can be used as the active ingredient for the brown adipocyte differentiation-inducing agent after the substance is modified by chemical modification or the like to thereby enhance the medicinal effect thereof. As a matter of course, even in the case when the substance has a sufficient medicinal effect, the substance may be subjected to similar modification for the purpose of further increasing the medicinal effect.

EXAMPLES

The following experiments were conducted so as to identify a molecule that acts on the induction of differentiation of brown adipocytes.

1. Search for Differentiation Inducing Factor for Brown Adipocytes

It is known that, when mice or rats are reared under a cold environment, the differentiation of brown adipocytes is stimulated and the amount of brown adipose tissues increase. Therefore, after C57BL6 mice were maintained under a 5° C. environment for 1 week (cold exposure), interscapular brown adipose tissues were collected and then a total RNA fraction was prepared. As a control, a total RNA fraction of the brown adipose tissues was prepared from mice that were not exposed to cold. Next, using cDNA synthesized from the total RNA fraction, the mRNA expression levels of UCP1 and Creg1 were measured by a quantitative PCR method. The results (n=4) that were normalized to the expression level of 36B4 mRNA measured in a similar manner as a control gene are shown in FIG. 1. As is reported previously, the brown adipose tissues developed due to exposure to cold, and the expression level of UCP1 gene increased to about 10-fold. Similarly, it was clarified that the expression level of Creg1 gene increased to 4-fold or more by exposure to cold.

2. Relationship Between Expression Levels of UCP1 and Creg1

Figure 2:
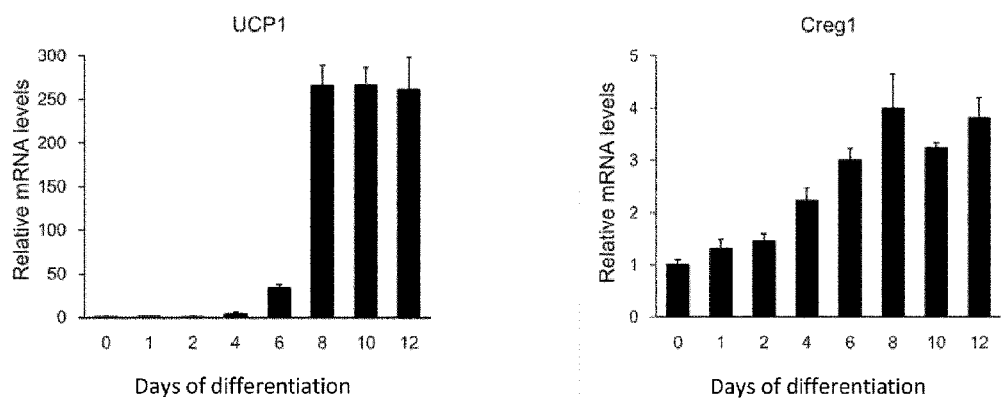
FIG. 2 shows the time course of the expression levels of UCP1 and Creg1 mRNAs in the differentiation of brown adipocytes. Left: the time course of the relative expression level of UCP1 mRNA, right: the time course of the relative expression level of Creg1 mRNA.

Subcutaneous white adipose tissues collected from C57BL6 mice were treated in a tissue digestive solution containing 0.2% collagenase at 37° C. for 30 minutes, and the tissue digestive solution was filtered by using two kinds (diameters: 70 μm and 40 μm) of nylon filters. The filtrate was centrifuged at 170 g for 6 minutes to give a precipitated cell fraction. These primary cells were then seeded onto a 24-well plate at 30,000 cells/well density, and cultured in a DMEM culture medium containing 10% fetal bovine serum (10% FBS/DMEM) in a 5% $CO_2$ incubator at 37° C. After two days, the culture medium was replaced with a differentiation culture medium (10% FBS/DMEM containing 0.5 mM of IBMX, 1 μM of dexamethasone, 10 μg/ml of insulin, 125 nM of indomethacin, 1 nM of T3 and 1 μM of Pioglitazone), thereby induce differentiation into brown adipocytes. Total RNA fractions were prepared from the cells on days 1, 2, 4, 6, 8, 10 and 12 with deeming the day before the induction of differentiation as day 0. Using the cDNA synthesized from the total RNA fraction, the mRNA expression levels of the UCP1 and Creg1 were measured by a quantitative PCR method. The results (n=3) that were normalized to the expression level of 36B4 mRNA measured in a similar manner as a control gene are shown in FIG. 2.

It was proved that the undifferentiated adipocyte progenitors included in the subcutaneous white adipose tissue were differentiated into brown adipocytes from about day 6 after the stimulation of induction of differentiation, from the change in the mRNA expression level of UCP1, which serves as a marker for the brown adipocytes. Furthermore, it was clarified that the mRNA expression level of Creg1 conformed well to the change in the UCP1 expression level, and increased along with the differentiation of the brown adipocytes.

Figure 3:
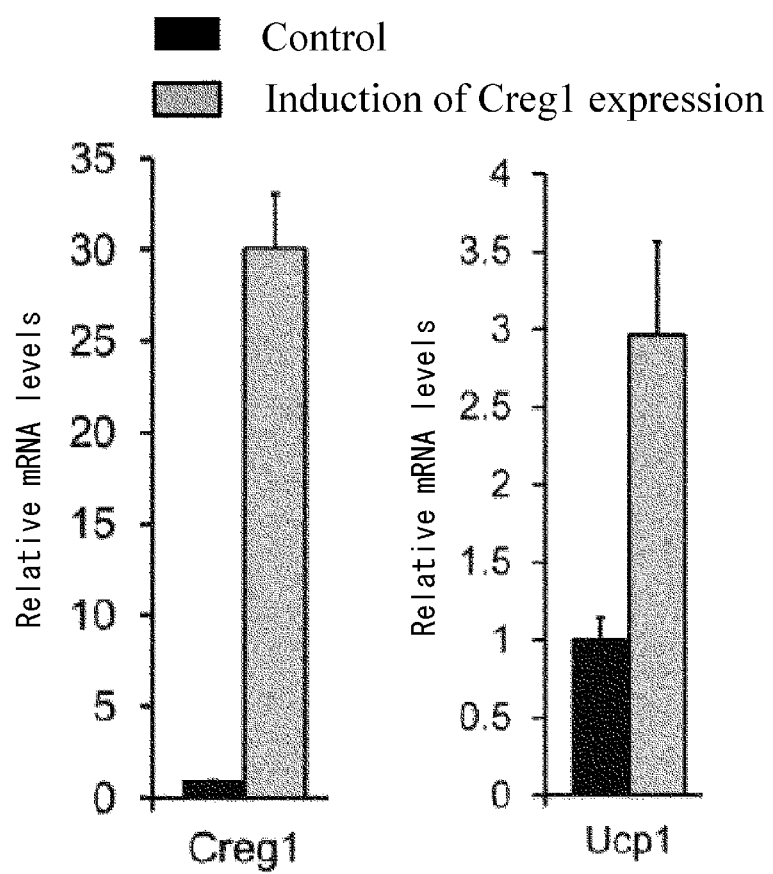
FIG. 3 shows the effect of induction of Creg1 expression on the differentiation of brown adipocytes. Left: the relative expression levels of Creg1 mRNA, right: the relative expression levels of UCP1 mRNA.

3. Examination of Effect of Creg1 Overexcession on Induction of Brown Adipocyte Differentiation In order to examine the effect of the overexpression of Creg1 on the induction of differentiation of the brown adipocytes, an experimental system using a retrovirus vector pMX was constructed. pMX-GFP (control) or pMX-Creg1 was transfected into PLAT-E cells, whereby each virus solution was made. Secondly, the virus solution was added to a primary progenitor adipocyte culture derived from subcutaneous white adipose tissues, which was prepared in advance in a similar manner to 2, the culture medium was replaced on the next day, and induction of differentiation into brown adipocytes was conducted. After 5 days, a total RNA fraction was prepared from the cells, and the mRNA expression levels of UCP1 and Creg1 were measured by a quantitative PCR method by using the synthesized cDNA. The results (n=6) that were normalized to the expression level of 36B4 mRNA measured in a similar manner as a control gene are shown in FIG. 3.

The expression level of Creg1 mRNA increased to about 30-fold of that of the control by the retroviral gene expression system. Furthermore, the UCP1 expression level increased to about 3-fold by the induction of expression of Creg1, and thus it was clarified that the induction of the differentiation of brown adipocytes was promoted.

4. Knockdown Experiment by siRNA

Figure 4:
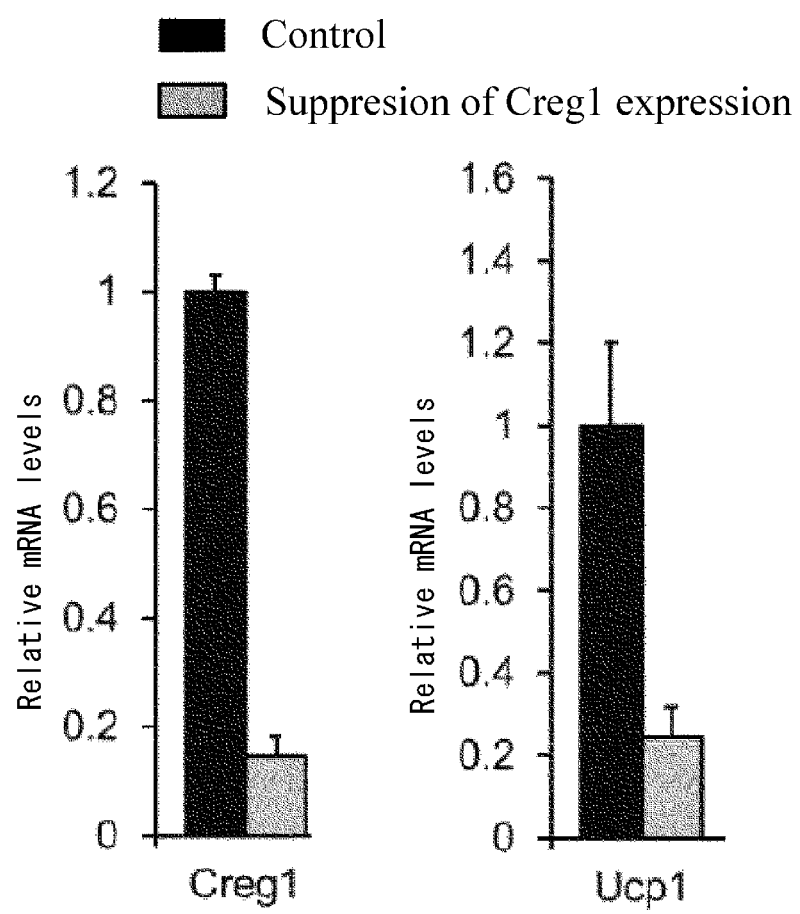
FIG. 4 shows the effect of suppression of Creg1 expression on the differentiation of brown adipocytes. Left: the relative expression levels of Creg1 mRNA, right: the relative expression levels of UCP1 mRNA.

A siRNA-mediated gene knockdown experiment of Creg1 was conducted by using a primary adipocyte progenitor culture derived from subcutaneous white adipose tissues was conducted in a similar manner to 2, whereby the effect on the induction of the differentiation of brown adipocytes was examined. Specifically, after the primary cells that were seeded on a 24-well plate had become about 50 to 70% confluent, Stealth RNAi for Creg1 knockdown of Invitrogen was introduced into the cells by using a Lipofectoamine RNAi MAX agent. On the next day, the culture medium was replaced, and induction of differentiation into brown adipocytes was conducted from day 2. After 5 days, a total RNA fraction was prepared from the cells, and the mRNA expression levels of UCP1 and Creg1 were measured by a quantitative PCR method by using a synthetic cDNA. The results (n=6) that were normalized to the expression level of 36B4 mRNA measured in a similar manner as a control gene are shown in FIG. 4.

By the gene knockdown by siRNA, the expression of Creg1 gene was decreased to 20% or less of that of the control. Similarly, the UCP1 expression level was decreased to about 20% of that of the control by the inhibition of the expression of Creg1, and thus it was clarified that the induction of the differentiation of the brown adipocytes was inhibited.

5. Effect of Creg1 In Vivo

Figure 5:
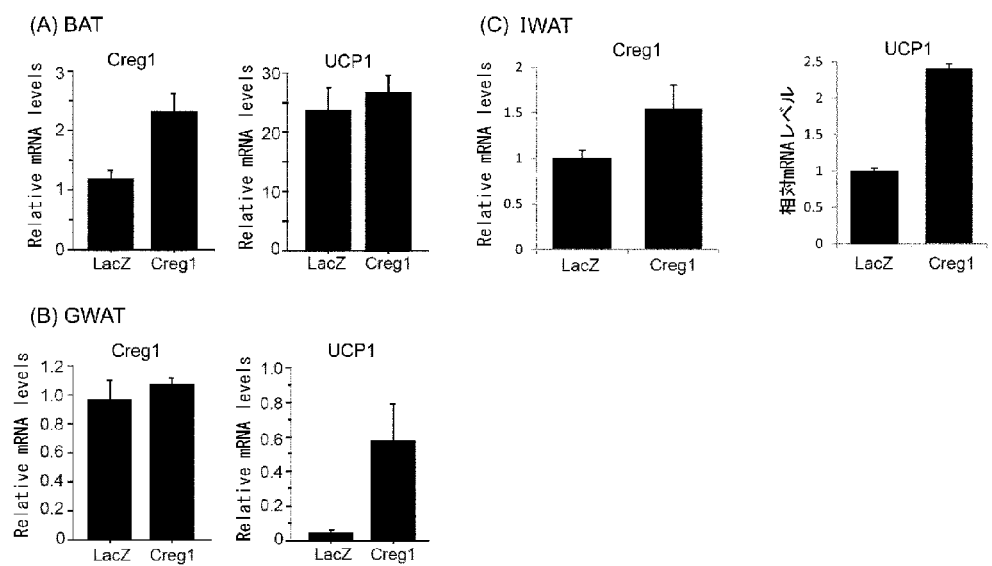
FIG. 5 shows the induction of brown adipocytes by the subcutaneous administration of Creg1-expressing adenovirus. (A) The relative expression level of Creg1 mRNA (left) and the relative expression level of UCP1 mRNA (right) in brown adipose tissues (BAT). (B) The relative expression level of Creg1 mRNA (left) and the relative expression level of UCP1 mRNA (right) in visceral white adipose tissues (GWAT). (C) The relative expression level of Creg1 mRNA (left) and the relative expression level of UCP1 mRNA (right) in inguinal white adipose tissues.

In order to verify the action of Creg1 gene on the differentiation of brown adipocytes in animal level, a Creg1 gene-expressing adenovirus vector system (Ad-Creg1) was constructed. Ad-LacZ (control) or Ad-Creg1 was transfected into 293A cells to produce adenovirus (about $3\times10^{10}$ pfu/20 µl), and the adenovirus was subcutaneously injected to mice. After one week, a total RNA fraction was prepared from each adipose tissue of the mice and the UCP1 mRNA level was measured by a quantitative PCR method by using a synthetic cDNA. The results (n=4) that were normalized to the expression level of 36B4 mRNA measured in a similar manner as a control gene are shown in FIG. 5. The Creg1 mRNA level in the brown adipose tissue of the mice administered with the Creg1-expressing adenovirus was about 2-fold as high as that of the control (A: BAT), whereas the increase of the UCP1 expression level was only about 15%. On the other hand, it was found that the increase of the Creg1 mRNA level in the visceral white adipose tissue (B: GWAT) was about 10%, whereas the UCP1 mRNA level was about 13-fold as high as that of the control. This result shows that the differentiation of the brown adipocytes was significantly induced in the visceral white adipose tissue. Furthermore, this induction of the differentiation of the brown adipocytes in the visceral white adipose tissue was also confirmed by a histological experiment (the result is abbreviated). Similarly, Ad-LacZ (control) or Ad-Creg1-expressing adenovirus (about $1.6\times10^9$ pfu/mouse) was injected into the inguinal white adipose tissue of mice, a total RNA fraction was prepared from the white adipose tissue at one week after the injection, and the UCP1 and 36B4 mRNA levels were measured by using a synthetic cDNA by a quantitative PCR method (n=4). The Creg1 mRNA level was about 1.6-fold as high as that of the control in the inguinal white adipose tissue (C: IWAT) of the mice administered with the Creg1-expressing adenovirus, and the UCP1 expression level increased to about 2.4-fold (FIG. 5 (C)). This result shows that the differentiation of the brown adipocytes was promoted by expressing Creg1 in the inguinal white adipose tissue.

Figure 6:
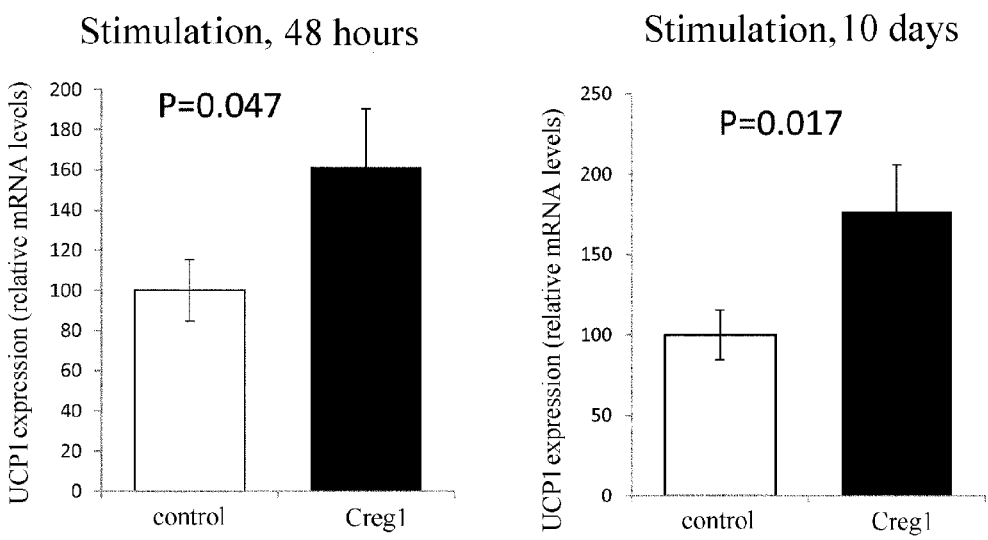
FIG. 6 shows the effect of Creg1 on the differentiation of brown adipocytes. Native Creg1 was added up to 48 hours (left) or 10 days (right) after the differentiation, and the mRNA expression level of UCP1 was measured.

6. Experiment of Adding Creg1 to Cells in Culture a) Preparation of Purified Creg1 Protein Murine Creg1 cDNA was inserted into a plasmid pcDNA3.1, which promotes protein expression in mammalian cells, and this Creg1 expression vector was introduced into simian kidney-derived Cos7 cells. In the Cos7 cells in which the Creg1 expression vector had been introduced, cells that stably produce murine Creg1 were selected and used as cells for preparing purified native Creg1 proteins. Secondly, these cells were subjected to mass-culture, and the Creg1 secreted in the obtained culture medium was purified, whereby native murine Creg1 protein was prepared. Furthermore, murine Creg1 cDNA was inserted into a plasmid pET-21, which promotes recombinant protein expression in *E. coli*, and this Creg1 expression vector was introduced into *E. coli*. The *E. coli* in which the Creg1 expression vector had been introduced was subjected to mass-culture, and the Creg1 was purified from the obtained culture medium, whereby recombinant murine Creg1 was prepared.

b) The effect of the native murine Creg1 on the induction of brown adipocyte differentiation was examined by using a murine fetus-derived C3H10 cell line (this can be differentiated into mesenchymal cells such as adipocytes). Specifically, C3H10 cells that had been seeded on a 12-well plate were cultured to confluence in a 10% FBS/DMEM growth culture medium. Subsequently, the culture medium was replaced with a differentiation culture medium to which 1 µM of native murine Creg1 had been added, and differentiation into brown adipocytes was induced. On day 10 after the induction of differentiation, a total RNA fraction was prepared from the cells. Using cDNA synthesized from the total RNA fraction, the expression level of UCP1 mRNA was measured by a quantitative PCR method. The results (n=3 to 6) that were normalized to the expression level of 36B4 mRNA measured in a similar manner as a control gene are shown in FIG. 6.

In either condition in which the native Creg1 protein was (1) added only for 48 hours after the initiation of differentiation culture, or (2) added up to 10 days after the initiation of differentiation culture, the mRNA expression level of UCP1, which serves as a marker of brown adipocytes, was significantly higher than that of the cells to which Creg1 was not added, and thus it was clarified that the differentiation of the brown adipocytes was promoted more strongly by the addition of the native Creg1 protein. On the other hand, a similar experiment was conducted by using recombinant murine Creg1 protein, but the recombinant Creg1 protein did not show the effect to promote brown adipocyte differentiation (the result is abbreviated). This result supports the function of Creg1 as a secreted protein, and suggests that Creg1 actually operates so as to promote the differentiation into brown adipocytes from the outside of the cells, probably through the receptors present on cell membranes. Furthermore, since the effect of recombinant Creg1 protein made by *E. coli* on brown adipocyte differentiation was not observed, it is considered that the modification with sugar chains that are added to Creg1 in cells is important for the function of Creg1.

7. Experiment for Inducing Expression of Creg1 in ApoE-Knockout Mouse Given a High Fat Diet Ad-LacZ (control) or Ad-Creg1 adenovirus was administered under anesthetic (about $1.5\times10^9$ pfu/mouse) to a 8-week old male ApoE-knockout arteriosclerosis model mouse from the tail vein, and the change in body weight over 2 weeks was observed under ingestion of a high fat diet. After 2 weeks, the mouse was sacrificed, and the respective tissues were collected. In this experiment, a method in which the expression of native Creg1 protein was induced in a living body by using an adenovirus vector was used as a substitute for a Creg1 protein administration experiment, and the effect thereof was examined in animal level. In this method, as the property of the adenovirus vector, the intended protein is produced mainly in the liver and then secreted into the blood. From the examination of tissue distribution of Creg1 gene expression in mice, it is considered that the liver is one of major organs for the production of Creg1, and thus this method using an adenovirus vector enhances the expression in the tissue in which Creg1 is originally produced. For the above-mentioned reason, it is expected that a similar result to that of an experiment in which Creg1 protein is administered is obtained in a method for inducing the expression of Creg1 using an adenovirus vector, in the purpose of increasing a Creg1 level in a living body, and thus the method can be considered to be an appropriate substitute experimental method at a laboratory level.

Figure 7:
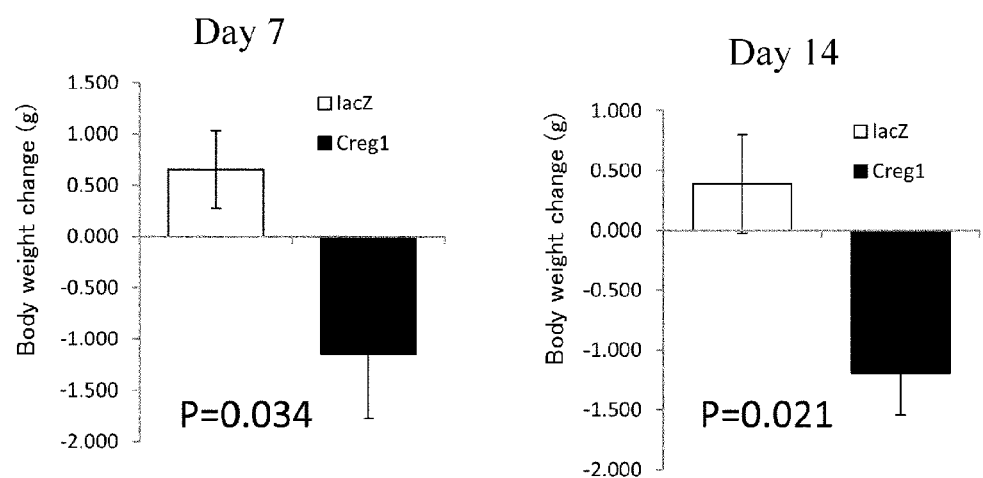
FIG. 7 shows the change of body weight in the Creg1-induced ApoE-knockout mice given a high fat diet. The body weight change in the mice expressing Creg1 induced by utilizing adenovirus was determined at day 7 (left) and day 14 (right).

The experimental results are shown in FIGS. 7 and 8. As a result of the observation of the change in body weight, it was clarified that the increase in body weight was significantly suppressed at day 7 and day 14 in mice in which the expression of Creg1 was induced, as compared to the control mice. Furthermore, also in the weights of the tissues collected at day 14, it was clarified that the tissue weights of the epididymal white adipose tissue (E-WAT) and retroperitoneal white adipose tissue (R-WAT), which are visceral fats, and of the liver, were significantly low in the Creg1-expressed mice as compared to those in the control mice (FIG. 8). In addition, the expression level of Creg1 mRNA in the liver at day 14 increased to about 1.4-fold (p<0.001) in Ad-Creg1 as compared to that in Ad-LacZ. These results show that the induction of Creg1 expression suppresses the accumulation of fats and prevents obesity in a metabolic syndrome model mice.

INDUSTRIAL APPLICABILITY

The brown adipocyte differentiation-inducing agent of the present invention can be utilized for the treatment or prevention of obesity, diabetes mellitus, lipid abnormality, arteriosclerosis, metabolic syndrome and the like.

The present invention is not limited at all to the embodiments for carrying out the invention and the explanations in Examples mentioned above. Various modified embodiments are also included in the present invention within a scope that can be easily conceived by a person skilled in the art without departing from the description of the claims. All of the contents of the articles, patent application publications and patents that are clearly indicated in the present specification are herein incorporated by reference.

The invention claimed is:

1. A method of treating a metabolic disorder or a related disease thereof, including a step of administrating a therapeutically effective amount of a medicament comprising the following (1) or (2) as an active ingredient to a patient with the metabolic disorders or the related disease thereof:
   (1) cellular repressor of E1A-stimulated genes 1 (CREG1) protein;
   (2) an expression vector encoding the CREG1 gene,
   wherein the metabolic disorders or related disease thereof is obesity, diabetes, lipid abnormality, arteriosclerosis, metabolic syndrome, or other disorders that would benefit from loss of weight.

2. The method according to claim 1, wherein the CREG1 protein comprises the amino acid sequence of SEQ ID NO: 1 or 2, or an amino acid sequence having at least 95% identity with the amino acid sequence of SEQ ID NO: 1 or 2.

3. The method according to claim 1, wherein the CREG1 gene comprises the nucleotide sequence of SEQ ID NO: 3, or a nucleotide sequence that encodes a protein having at least 95% identity with the amino acid sequence of SEQ ID NO: 1 or 2.

4. The method of claim 1, wherein the expression vector is a nonvirus vector.

5. The method of claim 4, wherein the nonvirus vector is a liposome.

6. The method of claim 5, wherein the liposome is a positively charged liposome or a Hemagglutinating virus of Japan liposome.

7. The method of claim 1, wherein the expression vector is a virus vector.

8. The method of claim 7, wherein the virus vector is selected from the group consisting of: an adeno-associated virus vector, a retrovirus vector, and a lentivirus vector.

9. The method of claim 1, wherein the medicament further comprises at least one of a carrier, an excipient, a disintegrating agent, a buffering agent, an emulsifying agent, a suspending agent, a soothing agent, a stabilizer, a preservative, an antiseptic, and a normal saline solution.

* * * * *